(12) United States Patent
Kanda et al.

(10) Patent No.: US 6,780,166 B2
(45) Date of Patent: Aug. 24, 2004

(54) IRRIGATION/ASPIRATION APPARATUS

(75) Inventors: Hidenori Kanda, Aichi (JP); Hideyuki Matsuda, Aichi (JP)

(73) Assignee: Nidek Co., Ltd., Aichi (JP)

( * ) Notice: Subject to any disclaimer, the term of this patent is extended or adjusted under 35 U.S.C. 154(b) by 188 days.

(21) Appl. No.: 09/775,613

(22) Filed: Feb. 5, 2001

(65) Prior Publication Data

US 2001/0023331 A1 Sep. 20, 2001

(30) Foreign Application Priority Data

Feb. 4, 2000 (JP) .................................... P2000-027019

(51) Int. Cl.$^7$ .......................... A61M 1/00; A61M 5/178
(52) U.S. Cl. ............................ 604/31; 604/27; 604/30; 604/35; 604/118; 604/119
(58) Field of Search ..................... 604/31–39, 21–26, 604/80–81, 27–32, 119, 122, 43–45, 48, 65–67, 93.01; 606/107, 166; 417/540

(56) References Cited

U.S. PATENT DOCUMENTS 5,810,765 A * 9/1998 Oda .............................. 604/31
6,283,937 B1 * 9/2001 Takamatsu et al. ........... 604/31

* cited by examiner

*Primary Examiner*—Brian L. Casler
*Assistant Examiner*—Roz Maiorino
(74) *Attorney, Agent, or Firm*—Sughrue Mion, PLLC

(57) ABSTRACT

An irrigation/aspiration apparatus for ophthalmic surgery, includes: an irrigation fluid supplying unit, which supplies irrigation fluid into a patient eye; an aspiration unit provided with a hand piece having an aspiration hole, which aspirates through the aspiration hole a removed tissue along with the irrigation fluid supplied into the patient eye; a pressure sensor which detects vacuum pressure caused by the aspiration unit; and a control unit connected to the irrigation fluid supplying unit and the pressure sensor, which varies at least one of irrigation rate and irrigation pressure by controlling the irrigation fluid supplying unit based on the detected vacuum pressure.

3 Claims, 5 Drawing Sheets

IRRIGATION/ASPIRATION APPARATUS

BACKGROUND OF THE INVENTION

The present invention relates to an irrigation/aspiration apparatus for use such as in a cataractal operation for extracting the opaque lens of the eye.

As a method of cataractal operation, phacoemulsification is generally practiced widely in which the lens nucleus is crushed and emulsified by causing a crushing tip to effect ultrasonic vibrations, and the emulsified lens nucleus tissue is aspirated from an aspiration hole at a distal end of the tip. In such an operation, an irrigation fluid is supplied into the patient's eye, and the drainage including the tissue particles and the residual cortex together with the supplied irrigation fluid is aspirated while maintaining the depth of the anterior chamber.

In recent years, a method called ultra-high vacuum phaco (UHVP) has come to be practiced in which vacuum pressure (aspiration pressure) is set to a high level for the purpose of the holding of the nucleus, the prevention of the rebound of the nucleus, the improvement of emulsification efficiency, and the like.

With such an operation, if the aspiration hole at the distal end of the tip is blocked by the lens nucleus and the like, and the vacuum pressure within an aspiration tube rises sharply, with the result that a phenomenon called a surge occurs. This is a phenomenon in which the supplied irrigation fluid in a quantity exceeding a set flow rate of aspiration (hereafter, referred to as aspiration rate) is transiently aspirated from the anterior chamber the moment the lens nucleus has been extracted. There are cases where, due to such a phenomenon, the replenishment of the irrigation fluid cannot catch up with the aspiration, making it impossible to maintain the depth of the anterior chamber. In particular, in UHVP in which the maximum vacuum pressure is set to a high level, the vacuum pressure within the aspiration tube is maintained at a higher level than usual, there is a tendency that the supplied irrigation fluid in a quantity exceeding the set aspiration rate is temporarily aspirated due to the surge, and the anterior chamber is likely to become crushed.

SUMMARY OF THE INVENTION

An object of the invention is to provide an irrigation/aspiration apparatus capable of maintaining the depth of the anterior chamber by the sufficient replenishment of the irrigation fluid with respect to the transient surge occurring when the blocked aspiration hole of the crushing tip is opened.

To overcome the above-described problems, the invention is characterized by having the following features.

(1) An irrigation/aspiration apparatus for ophthalmic surgery, comprising:

an irrigation fluid supplying unit, which supplies irrigation fluid into a patient eye;

an aspiration unit provided with a hand piece having an aspiration hole, which aspirates through the aspiration hole a removed tissue along with the irrigation fluid supplied into the patient eye;

a pressure sensor which detects vacuum pressure caused by the aspiration unit; and a control unit connected to the irrigation fluid supplying unit and the pressure sensor, which varies at least one of irrigation rate and irrigation pressure by controlling the irrigation fluid supplying unit based on the detected vacuum pressure.

(2) The apparatus of (1), wherein the control unit controls the irrigation fluid supplying unit such that at least one of the irrigation rate and irrigation pressure is increased as the vacuum pressure is increased, and at least one of the irrigation rate and the irrigation pressure is decreased as the vacuum pressure is decreased.

(3) The apparatus of (1), wherein the control unit controls the irrigation fluid supplying unit such that at least one of the irrigation rate and the irrigation pressure is increased if a first predetermined vacuum pressure higher than a basic vacuum pressure is detected, and at least one of the irrigation rate and irrigation pressure is decreased if a second predetermined vacuum pressure lower than the first vacuum pressure, or the basic vacuum pressure is detected.

(4) The apparatus of (3), wherein the control unit controls the irrigation fluid supplying unit such that at least one of the irrigation rate and irrigation pressure is decreased when a predetermined time period is elapsed after the second vacuum pressure is detected.

(5) The apparatus of (3), further comprising:

a setting unit which sets at least one of the irrigation rate and irrigation pressure under the basic vacuum pressure, and which is connected to the control unit.

(6) The apparatus of (1), wherein:

the irrigation fluid supplying unit includes an irrigation bottle containing the irrigation fluid, a supporting member supporting the irrigation bottle, and a vertically moving mechanism which vertically moves the supporting member within a predetermined height range and which is connected to the control unit;

the control unit controls driving of the vertically moving mechanism based on the detected vacuum pressure.

(7) The apparatus of (1), wherein the aspiration unit includes an aspiration tube connected to the hand piece, and a pump which generates the vacuum pressure within the aspiration tube.

(8) The apparatus of (1), wherein:

the irrigation fluid supplying unit includes an irrigation tube, and a control valve which controls at least one of the irrigation rate and the irrigation pressure within the irrigation tube and which is connected to the control unit, and the control unit controls the control valve based on the detected vacuum pressure.

The present disclosure relates to the subject matter contained in Japanese patent application No. 2000-27019 (filed on Feb. 4, 2000), which is expressly incorporated herein by reference in its entirety.

DESCRIPTION OF THE PREFERRED EMBODIMENT

Figure 1:
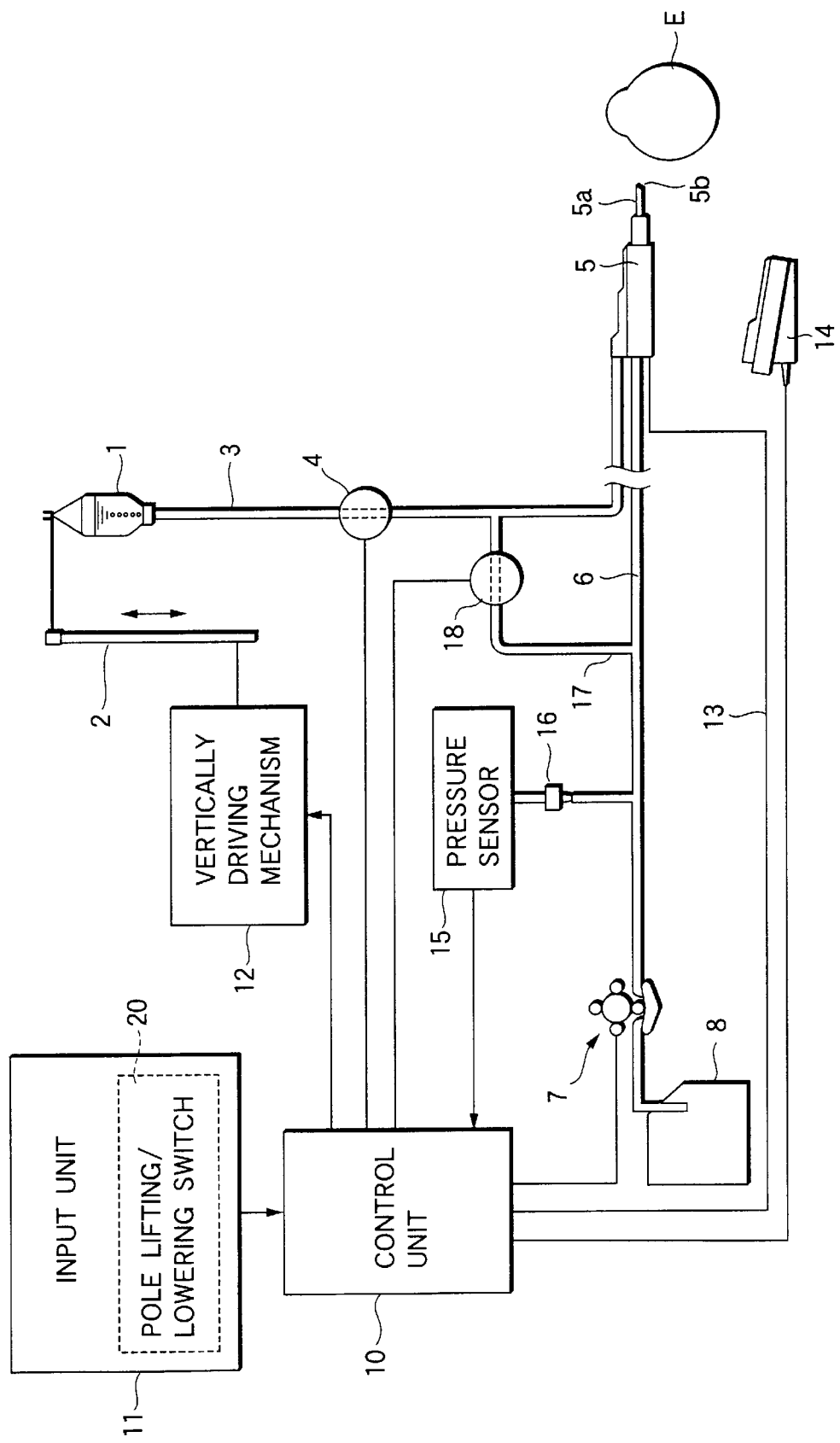
FIG. 1 is a schematic diagram of an irrigation/aspiration apparatus in accordance with an embodiment of the invention.

Referring now to the accompanying drawings, a description will be given of an embodiment of the invention. FIG. 1 is a schematic diagram of an irrigation/aspiration apparatus in accordance with the embodiment.

An irrigation bottle 1 which is filled with an irrigation fluid such as a physiological saline solution is suspended from a pole 2. The pole 2 is supported on an unillustrated main unit of the apparatus so as to be vertically movable, and is vertically moved by a vertically driving mechanism 12. It is possible to use various types of mechanism as the vertically driving mechanism 12. For example, it is possible to use a mechanism in which a rack provided on the pole 2 is vertically moved, a mechanism in which a rotating shaft of a motor and the pole 2 are threadedly engaged with each other by a feed screw, or the like. The height of the bottle 1 is changed by the vertical movement of the pole 2, whereby the flow rate of irrigation (hereafter, referred to as irrigation rate) (=irrigation pressure or irrigation speed) of the irrigation fluid which drops from the bottle 1 can be adjusted.

The irrigation fluid from the bottle 1 passes through an irrigation tube 3, and is supplied to the patient's eye E through an operating hand-piece 5 gripped by the operator. A control valve 4 is provided midway in the irrigation tube 3, and the flow control (regulation) of the irrigation fluid is effected by the opening or closing of the control valve 4 under or through control by a control unit 10. In this embodiment, as the hand-piece 5, a US hand-piece is used for crushing and emulsifying the lens nucleus which became opaque and hardened due to cataract by ultrasonic vibrations of a crushing tip 5a and by aspirating it from an aspiration hole 5b at a distal end of the tip 5a. The ultrasonic vibration of the tip 5a is effected as the control unit 10 supplies electric power to an ultrasonic vibrator provided in the hand-piece 5 through a power cable 13.

A flexible aspiration tube 6 is connected to the hand-piece 5, and a peristaltic pump 7 and a connecting portion 16 leading to a pressure sensor 15 are provided midway therein. Further, the aspiration tube 6 communicates with the irrigation tube 3 through a bypass tube 17, and the flow control (regulation) of the bypass tube 17 is effected by a control valve 18. The pressure sensor 15 constantly detects the vacuum pressure within the aspiration tube 6, and sends the result of detection to the control unit 10. When the rise of the vacuum pressure from a set value has been detected, the control valve 18 is opened, as required, under or though control by the control unit 10, and the irrigation fluid is allowed to flow into the aspiration tube 6 from the irrigation tube 3 through the bypass tube 17 so as to lower the vacuum pressure. An upper limit (maximum vacuum pressure) and the like of the vacuum pressure are set by the switching operation of an input unit 11.

The supplied irrigation fluid and the removed tissue are aspirated from the aspiration hole 5b, and are discharged into a drainage bag 8 through the aspiration tube 6. The control unit 10 controls the flow rate of aspiration or vacuum rate (hereafter, referred to as aspiration rate) and the vacuum pressure (aspiration pressure) by controlling the drive of the pump 7 on the basis of the position signal based on the stepping position of a foot switch 14 as well as a set value from the input unit 11.

A description will be given hereafter of the operation of the irrigation/aspiration apparatus having the above-described construction. In this embodiment, a description will be given of a cataractal operation (phacoemulsification) in which the opaque lens is emulsified by the US hand-piece 5 with ultrasonic vibrations and is aspirated.

At the time of the surgery, the operator effects preparation necessary for the operation such as the attachment of the various tubes and the like, and effects such as the setting of the irrigation rate, the maximum vacuum pressure, and the aspiration rate by operating the input unit 11. The setting of the irrigation rate is effected as the operator operates a pole lifting/lowering switch 20 of the input unit 11. The control unit 10 adjusts the height of the bottle 1 by driving the vertically driving mechanism 12 on the basis of the signal from the switch 20.

After the operator has incised the sclera and the anterior capusule while observing the eye E with a surgical microscope, the operator steps on the foot switch 14 up to a position for effecting the irrigating operation. The control unit 10 allows the irrigation fluid to flow out by opening the control valve 4 on the basis of the signal from the foot switch 14. Then, when the irrigation fluid is supplied into the anterior chamber of the eye E by inserting the tip 5a of the hand-piece 5 into the eye E, the height of the bottle 1 is adjusted so as to appropriately secure the depth of the anterior chamber.

After securing the depth of the anterior chamber by supplying the irrigation fluid, the operator steps on the foot switch 14 up to the position for effecting the aspirating operation in addition to the irrigating operation, so as to effect the aspiration. The control unit 10 drives the pump 7 to aspirate the supplied irrigation fluid at a set aspiration rate on the basis of the signal from the foot switch 14. The vacuum pressure occurring due to the aspiration of the supplied irrigation fluid corresponding to a set aspiration rate in the state in which the aspiration hole 5b is open will be referred to as the basic vacuum pressure, and the supplied irrigation fluid in the anterior chamber is aspirated through the aspiration hole 5b on the basis of this basic vacuum pressure.

The operator further steps on the foot switch 14 up to a position for effecting the ultrasonic vibration operation in addition to the irrigating and aspirating operation, so as to emulsify and crush the lens nucleus. The control unit 10, in turn, causes the tip 5a of the hand-piece 5 to generate ultrasonic vibrations on the basis of the signal from the foot switch 14.

When the aspiration hole 5b is blocked by the lens nucleus during the aspiration, the vacuum pressure within the aspiration tube 6 rises due to this blockage and becomes higher than the basic vacuum pressure. In this state, if the occlusions such as the lens nucleus are removed by the emulsification and aspiration of the lens nucleus due to the ultrasonic vibration of the tip 5a, the supplied irrigation fluid in a quantity exceeding the set aspiration rate is temporarily aspirated from the anterior chamber (surge) because of the effect of the vacuum pressure which became higher than the basic vacuum pressure. For this reason, to stabilize the depth of the anterior chamber at this time, the control unit 10 controls the height of the bottle 1 so as to vary the irrigation rate.

Hereafter, a description will be given of a controlling method for varying the irrigation rate with reference to FIG. 2 which schematically illustrates the relationship between the height of the bottle 1, on the one hand, and the aspiration rate and the vacuum pressure, on the other hand. It should be noted it is assumed that the conditions which are set include the aspiration rate of 30 ml/min, the maximum vacuum pressure of 40 kPa (approx. 300 mmHg), and the bottle height of 65 cm. Further, the basic vacuum pressure corresponding to the set aspiration rate of 30 ml/min is set to 7 kPa (approx. 52 mmHg), such that a sufficient quantity of irrigation fluid will be replenished (irrigated) with respect to the set aspiration rate of 30 ml/min by the irrigation rate in the case where the height of the bottle 1 is 65 cm.

Figure 2:
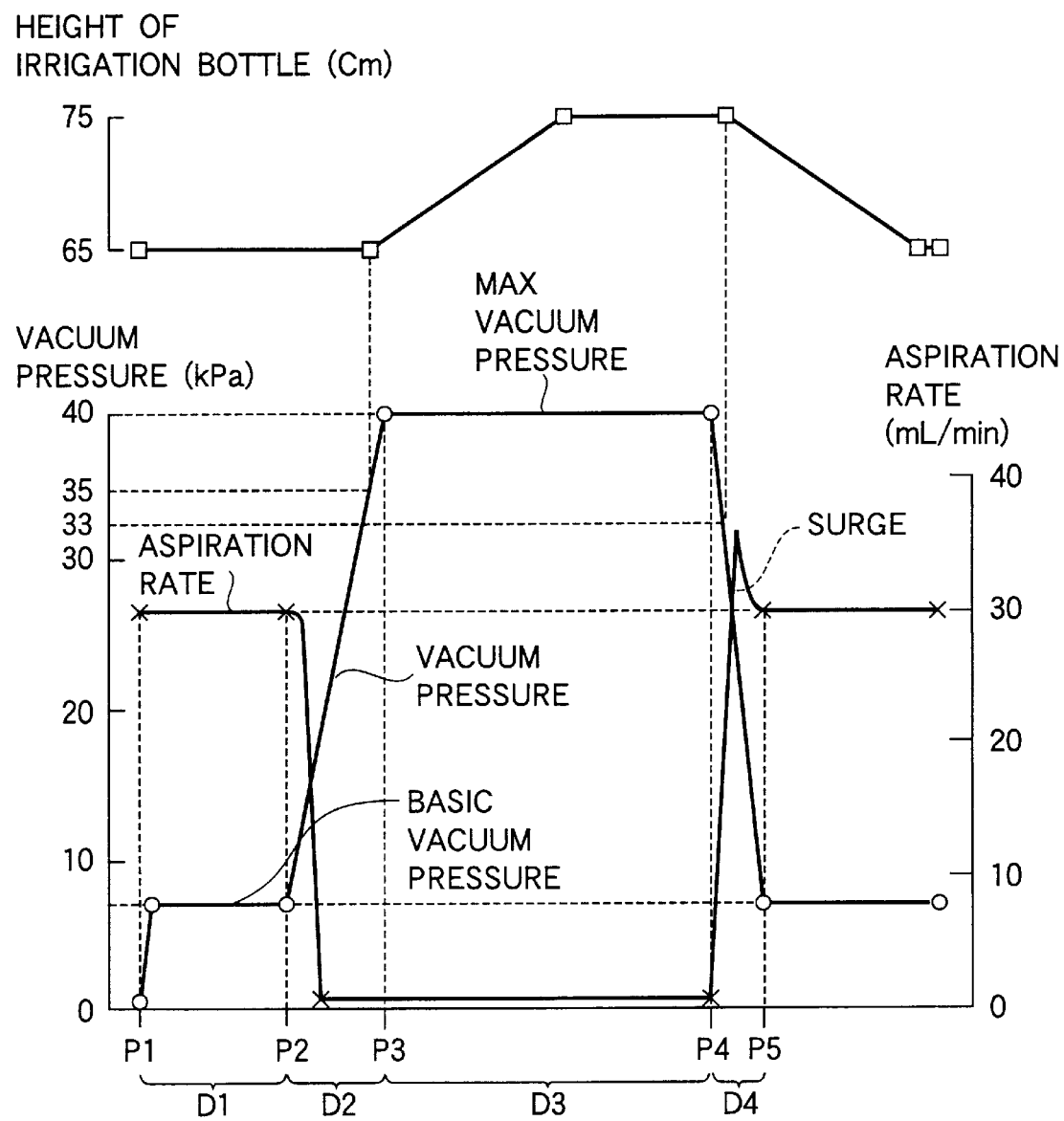
FIG. 2 is an explanatory diagram of the relationship between the height of an irrigation bottle, on the one hand, and a flow rate of irrigation and vacuum pressure, on the other hand, during a surgical operation.

In FIG. 2, in the section D1 from the point of time P1 of aspiration start until the point of time P2 when part of the aspiration hole 5b begins to be blocked, the irrigation fluid is supplied into the anterior chamber with the aspiration rate of 30 ml/min (basic vacuum pressure of 7 kPa), and the irrigation fluid at a rate based on the bottle height of 65 cm is supplied so that the irrigation fluid corresponding thereto will be replenished, thereby maintaining the depth of the anterior chamber.

In the section D2 from the point of time P2 of the start of blocking of the aspiration hole 5b until the point of time P3 when the maximum vacuum pressure is reached, the vacuum pressure within the aspiration tube 6 rises sharply. The rate of increase (gradient) of the vacuum pressure at this time is dependent on the set aspiration rate (the rotational speed of the pump 7). When it is detected by the pressure sensor 15 that the maximum vacuum pressure of 40 kPa has been reached, the control unit 10 stops the rotation of the pump 7, thereby maintaining the vacuum pressure within the aspiration tube 6 at the maximum vacuum pressure.

In the section D2 when the vacuum pressure rises, the control unit 10 causes the bottle 1 to be raised by the vertically driving mechanism 12 in correspondence with the vacuum pressure detected by the pressure sensor 15 so as to set the irrigation rate higher than the initial set value. Here, as the height of the bottle 1, a height is required which makes it possible to replenish the irrigation fluid without a delay with respect to at least the portion of the aspiration rate which increases sharply due to the surge. (The higher the vacuum pressure when the aspiration hole 5b has been opened, the higher the aspiration rate which increases sharply due to the surge.) In this embodiment, it is ensured that the depth of the anterior chamber can be sufficiently maintained during the surge at the initially set bottle height of 65 cm until the vacuum pressure of 35 kPa. When the vacuum pressure has exceeded 35 kPa, the height of the bottle 1 is raised to 75 cm to increase the rate of irrigation fluid supplied into the eye E.

In the section D3 from the point of time P3 when the maximum vacuum pressure is reached until the point of time P4 when the aspiration hole 5b is opened, since the aspiration hole 5b is completely blocked, the aspiration rate is practically nil, so that the lens nucleus can be firmly held under the maximum vacuum pressure. Consequently, even if powerful ultrasonic vibrations are applied to the tip 5a, the lens nucleus is not dislocated from the distal end of the tip 5a, and the crushing and emulsification can be performed efficiently.

From the point of time P4 of the opening of the aspiration hole 5b, the aspiration rate increases sharply, and the surge occurs, but the surge ceases in the vicinity of the point of time P5 when the vacuum pressure has dropped to the basic vacuum pressure. Subsequently, the aspiration rate returns to the set aspiration rate.

During the section D4 from the point of time P4 of the opening of the aspiration hole 5b until the point of time P5 when the vacuum pressure drops to the basic vacuum pressure, the control unit 10 lowers the bottle 1 to the position of the initially set height of 65 cm in conjunction with the decline of the vacuum pressure. As for the timing of its lowering, the pole 2 is lowered when the vacuum pressure has dropped below a threshold, e.g., 33 kPa, of vacuum pressure lower than the vacuum pressure of 35 kPa for raising the bottle 1. In a case where the height of the bottle 1 is changed from 75 cm to 65 cm by the vertically driving mechanism 12 as explained in this embodiment, several seconds or thereabouts is required as the time for this change. Even if the lowering operation of the bottle 1 is started before the occurrence of the surge, in the very short time when the surge occurs (0.1 second or thereabouts from P4), the height of the bottle 1 is only slightly lowered from 75 cm, and since a sufficient irrigation rate is being imparted with respect to the sharp aspiration rate due to the surge, the irrigation fluid is replenished sufficiently in a quantity corresponding to the aspirated portion, thereby making it possible to maintain the depth of the anterior chamber.

The lowering of the bottle 1 at the point of time P4 of the opening of the aspiration hole 5b may be effected subsequent to the point of time P5 when the surge ceases, but if an excess irrigation rate is imparted with respect to the basic vacuum pressure, the intraocular pressure become high, which is undesirable for the eye E. In this embodiment, therefore, to minimize the period of time when the intraocular pressure is high, lowering control is provided which takes into account the driving time of the vertically driving mechanism 12.

Thus, after the irrigation rate is increased to allow a sufficient irrigation fluid to be replenished with respect to the surge occurring when the blocked aspiration hole 5b has been opened, when the bottle 1 has returned to the basic vacuum pressure and aspiration is being effected stably, the height of the bottle 1 is lowered to apply an appropriate irrigation rate. Consequently, it is possible to maintain the depth of the anterior chamber even during the surge without subjecting the eye E to high ocular pressure for a long time.

Although, in the foregoing description, the height of the bottle 1 is changed between two heights of 65 cm and 75 cm, the number of thresholds for vacuum pressure for changing the height of the bottle 1 may be increased to allow the change of the irrigation rate in a multiplicity of stages.

Still further, in a case where an irrigation-rate varying mechanism is provided which is sufficiently capable of following the change of the irrigation rate in correspondence with the change of the vacuum pressure, control may be provided so as to allow the irrigation rate to be constantly changed in correspondence with the change of the vacuum pressure. In this case, in the process in which the vacuum pressure increases due to the blockage of the aspiration hole 5b, the irrigation rate is changed at the same timing as the rise in the vacuum pressure, whereas, in the process in which the vacuum pressure drops, the irrigation rate is decreased by providing a delay time which takes into consideration the portion of the time from the point of time of the opening of the blocked aspiration hole 5b until the occurrence of the surge, or the irrigation rate is decreased at the point of time when the vacuum pressure has returned substantially to the basic vacuum pressure.

Figure 3:
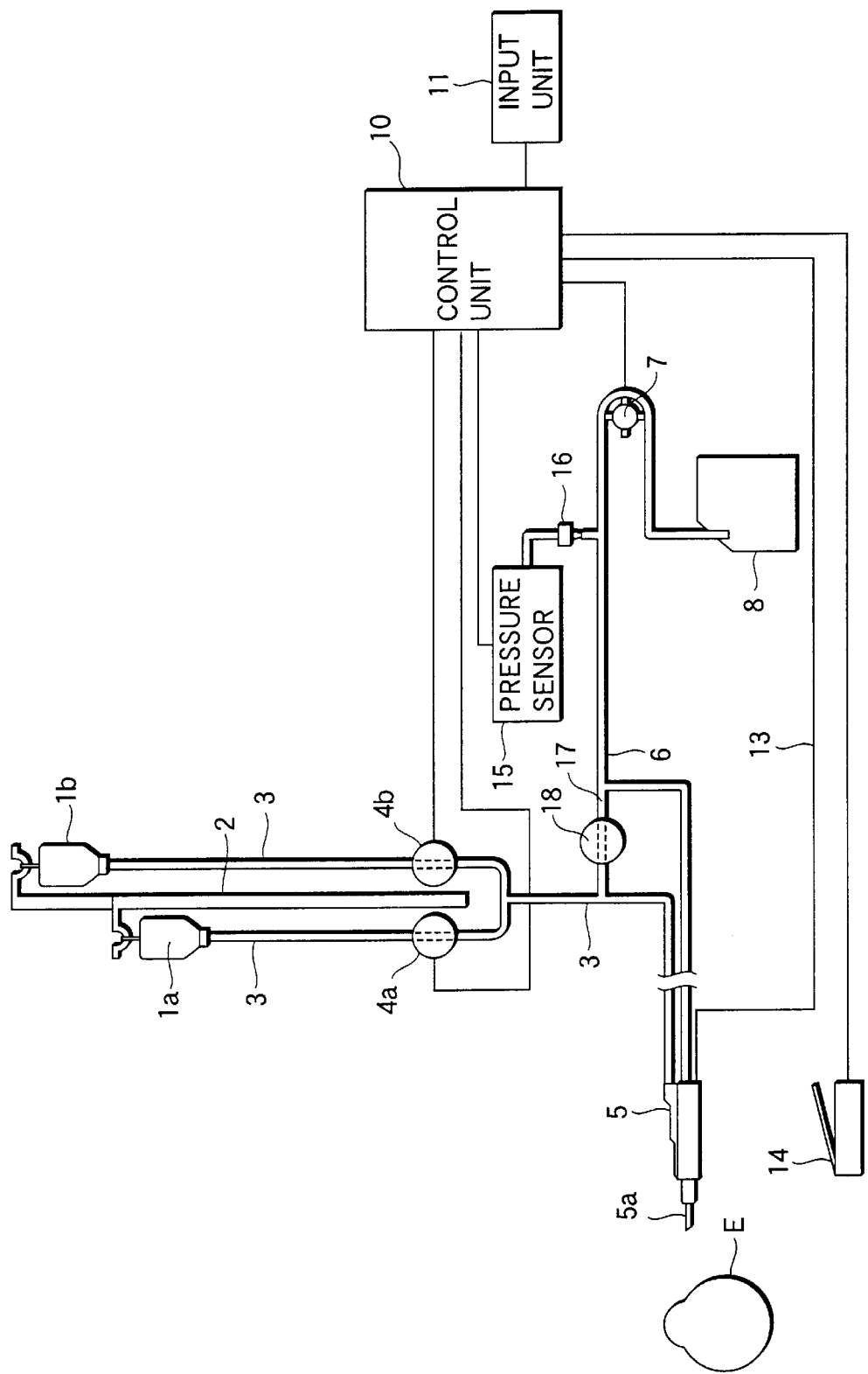
FIG. 3 is a schematic diagram showing a modification 1 for the irrigation/aspiration apparatus in accordance with the embodiment of the present invention.
Figure 4:
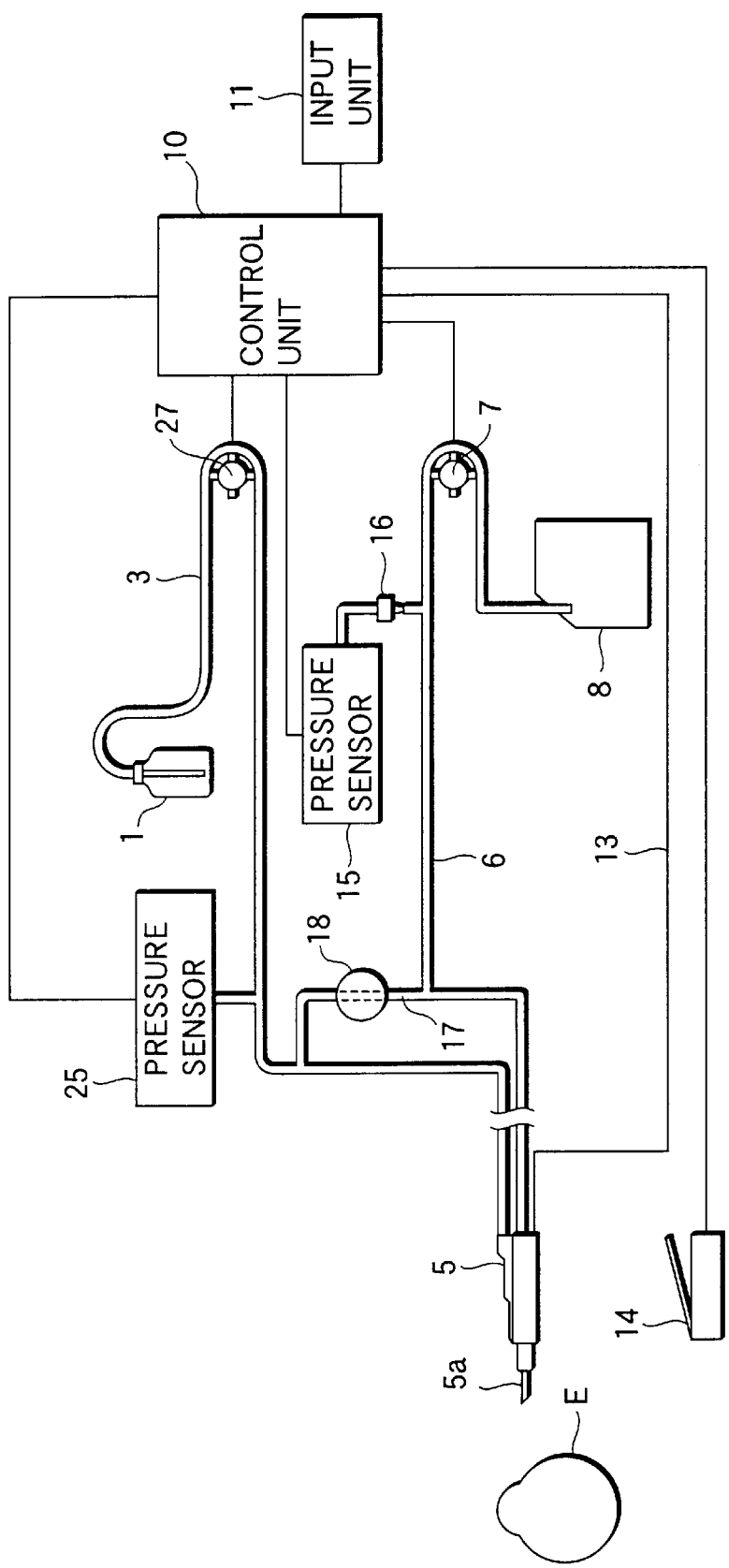
FIG. 4 is a schematic diagram showing a modification 2 for the irrigation/aspiration apparatus in accordance with the embodiment of the present invention.
Figure 5:
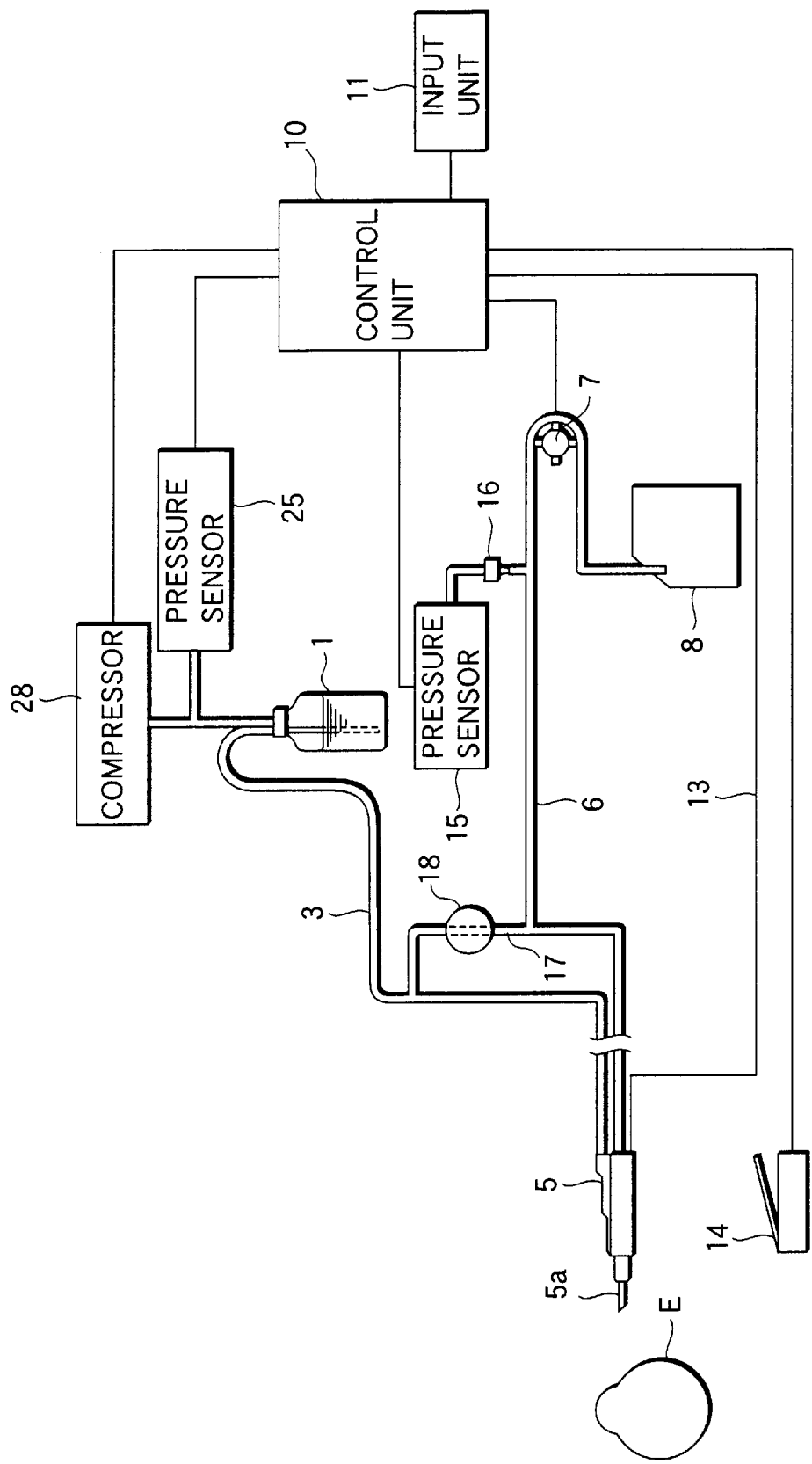
FIG. 5 is a schematic diagram showing a modification 3 for the irrigation/aspiration apparatus in accordance with the embodiment of the present invention.

In addition, although, in the above-described embodiment, the irrigation rate is changed by vertically moving the bottle 1, the irrigation rate may be regulated by controlling the efflux of the irrigation fluid from a plurality of irrigation bottles 1a and 1b having different heights by means of the control valves 4a and 4b (see FIG. 3). Further, it is also possible to effect the regulation of the irrigation rate by supplying the irrigation fluid by a pump 27, a compressor 28 or the like (see FIG. 4 and FIG. 5). In case where the irrigation rate is adjusted by the pump 27 and the compressor 28, a pressure sensor 25 is provided for detecting an irrigation pressure, and the control unit 10 controls the pump 27 and the compressor 28 based on the detected irrigation pressure.

For example, in a case where control of efflux by the control valves 4a and 4b is effected by providing irrigation bottles 1a and 1b at 65 cm and 75 cm, respectively, since there is virtually no time lag, the timing for changeover from 75 cm to 65 cm, unlike the foregoing example, is preferably effected after the lapse of a predetermined time (since the time duration from the point of time P4 until the occurrence of the surge is 0.1 second or thereabouts, it is sufficient to set this time) from the point of time when the decline of the vacuum pressure below 33 kPa has been detected. Alternatively, the changeover may be effected when the vacuum pressure has returned substantially to the basic vacuum pressure. In addition, three or more bottles having respective different heights can be used in the present invention.

As described above, in accordance with the invention, it is possible to perform a surgical operation in which the maximum vacuum pressure is set to a high level while suppressing the crushing of the anterior chamber due to the surge when the blocked aspiration hole of the crushing tip is opened. In addition, it is possible to carry out the operation without increasing the intraocular pressure during aspiration under the basic vacuum pressure.

What is claimed is:

1. An irrigation/aspiration apparatus for ophthalmic surgery, comprising:

an irrigation fluid supplying unit, including a changing unit that changes an irrigation rate of irrigation fluid to be supplied into a patient eye;

an aspiration unit provided with a hand piece having an aspiration hole, an aspiration tube connected to the hand-piece, and a pump that generates vacuum pressure within the aspiration tube, the aspiration unit aspirating removed tissue along with the irrigation fluid supplied into the patient eye through the aspiration hole and the aspiration tube by the generated vacuum pressure;

a pressure sensor that detects the vacuum pressure within the aspiration tube; and a control unit connected to the changing unit and the pressure sensor, that increases and decreases the irrigation rate during aspiration by controlling operation of the changing unit based on the detected vacuum pressure, wherein the control unit operates the changing unit so that the irrigation rate is a first set irrigation rate in a normal state, operates the changing unit so that the irrigation rate is a second set irrigation rate higher than the first set irrigation rate when the pressure sensor detects that the vacuum pressure exceeds a limit value at which a depth of an anterior chamber of the patient eye is held while maintaining the first set irrigation rate against a phenomenon in which an aspiration rate generated when an occlusion of the aspiration hole is removed rises sharply, and operates the changing unit so that the irrigation rate is returned from the second set irrigation rate to the first set irrigation rate when the pressure sensor detects that, after reaching at the second set irrigation rate, the vacuum pressure becomes less than a predetermined value which is set lower than a maximum vacuum pressure.

2. The apparatus of claim 1, wherein:

the irrigation fluid supplying unit includes an irrigation bottle containing the irrigation fluid, and a supporting member supporting the irrigation bottle;

the changing unit includes a vertically moving mechanism that vertically moves the supporting member within a predetermined height range and that is connected to the control unit; and the control unit controls driving of the vertically moving mechanism based on the detected vacuum pressure.

3. The apparatus of claim 1, wherein:

the irrigation fluid supplying unit includes an irrigation tube;

the changing unit includes a control valve that controls the irrigation rate within the irrigation tube and that is connected to the control unit, and the control unit controls operation of the control valve based on the detected vacuum pressure.

* * * * *